(12) United States Patent
Mittermeyer et al.

(10) Patent No.: US 7,883,492 B2
(45) Date of Patent: Feb. 8, 2011

(54) CATHETER WITH PORTIONS THAT CAN CHANGE IN VOLUME

(75) Inventors: Stephan Mittermeyer, Landshut (DE); Andreas Hartlep, Holzkirchen (DE)

(73) Assignee: BrainLAB AG, Feldkirchen (DE)

(*) Notice: Subject to any disclaimer, the term of this patent is extended or adjusted under 35 U.S.C. 154(b) by 39 days.

(21) Appl. No.: 12/049,534

(22) Filed: Mar. 17, 2008

(65) Prior Publication Data

US 2008/0228140 A1   Sep. 18, 2008

Related U.S. Application Data

(60) Provisional application No. 60/908,520, filed on Mar. 28, 2007.

(30) Foreign Application Priority Data

Mar. 16, 2007   (EP)   ................... 07005470

(51) Int. Cl.
*A61M 29/00*   (2006.01)

(52) U.S. Cl. ................................ 604/104

(58) Field of Classification Search ................ 604/104, 604/264, 256, 530; 600/585; 427/2.1
See application file for complete search history.

(56) References Cited

U.S. PATENT DOCUMENTS

| 5,135,501 A | * | 8/1992 | Cameron | 604/161 |
| 5,573,520 A | * | 11/1996 | Schwartz et al. | 604/526 |
| 2003/0023190 A1 | | 1/2003 | Cox | |
| 2006/0116636 A1 | * | 6/2006 | Murphy et al. | 604/104 |

FOREIGN PATENT DOCUMENTS

WO   WO 2006/060181   6/2006

* cited by examiner

*Primary Examiner*—Nicholas D Lucchesi
*Assistant Examiner*—Brooke M Matney
(74) *Attorney, Agent, or Firm*—Renner, Otto, Boisselle & Sklar, LLP

(57) ABSTRACT

A catheter for administering a substance into body tissues includes an elongated catheter body that has at least one portion of the length of the catheter body that expands after the catheter is inserted in the patient's body. The portion that expands provides a seal against backflow of the substance along the outer surface of the catheter body and away from the intended treatment area.

16 Claims, 1 Drawing Sheet

CATHETER WITH PORTIONS THAT CAN CHANGE IN VOLUME

RELATED APPLICATION DATA

This application claims priority of U.S. Provisional Application No. 60/908,520 filed on Mar. 28, 2007, and EP 07005470 filed on Mar. 16, 2007, which are incorporated herein by reference in their entirety.

FIELD OF THE INVENTION

The invention relates to a catheter for administering a substance into a body tissue. Such catheters may be introduced through the cranium into the brain tissue in neurosurgical procedures to release a substance directly in the brain tissue.

BACKGROUND OF THE INVENTION

One disadvantage of previous catheters is that during infusion of a liquid substance into a target tissue, the liquid substance may flow back along the outer wall of the catheter due to a pressure of the liquid in an administering region between the outer wall of the catheter and the adjacent body tissue. This backward flow in the space or gap between the outer wall of the catheter and the body tissue at a distal end of the catheter (the end that is inserted into the patient) is also referred to as backflow. When such backflow is present, computer-assisted simulation of a dispersion of the liquid in the adjacent brain tissue can be inaccurate. In such a simulation, the distal end of the catheter is ordinarily modelled as a point source. In reality, rather than a point source, the liquid substance is dispersed along the catheter in an indeterminable way.

The liquid substance may also exit the brain tissue through the space or gap between the catheter's outer wall and the body tissue. Exiting through this gap is possible when the distal end of the catheter is placed near an outer cerebral membrane without adequate sealing or if it is crossing a sulci. The escape of the liquid substance may adversely affect treatment. A seal may be attached to the outer wall of the catheter, however, such a seal may be obstructive or even damaging to the tissue while the catheter is inserted into the patient. An injury from the seal (rigid or otherwise) also could cause channels in the brain tissue. The liquid substance intended to be administered for treatment may escape from the administering region through these channels. Thus, when compared to the simulated dispersion that assumes a point source for the administered substance, the actual substance dispersions in the patient may have an undesirable deviation. For the simulation to match the treatment, it is advantageous to limit the backflow to a minimum. This also may allow the surgeon greater freedom in trajectory planning.

US Publication No. 2006/0116636 A1 discloses a catheter in which the distal end includes a coating that increases the catheter's volume in the presence of a liquid. This "swelling" may be used to create a seal between an outer wall of the catheter and the adjacent brain tissue. In a swelled state, however, the affected region of said catheter exhibits a smooth outer wall. Because the brain tissue is irregular in structure and the swollen region of the catheter has a smooth outer wall, the liquid to be administered may penetrate through fine channels between the swollen region and the brain tissue. Such liquid may flow past the seal towards the proximal end (handle end) of the catheter.

SUMMARY OF THE INVENTION

A catheter in accordance with the invention is configured for administering a substance into a body tissue (e.g., brain structures or any other target body tissue), such that the catheter's volume can change in response to ambient conditions. The catheter may have an elongated catheter body that surrounds one or more lumens. One or more partial portions of a length of the catheter body may include a material that changes its volume in response to changes in the ambient conditions in the administering environment. In use, the volume change in the material may produce a profiled outer surface of the catheter.

In other words, after the catheter has been introduced into body tissue, defined regions or partial portions of an outer wall of the catheter may change in volume. The partial portions of the catheter may partially or completely consist of a material that changes volume (e.g., a biocompatible hydrogel polymer). Such a catheter may effectively prevent a backward flow of the substance or liquid between the outer wall of the catheter and the adjacent body tissue.

The profile of the outer surface of the catheter (e.g., a stepped profile) may have a plurality of bumps along the catheter axis that form a plurality of sealing portions. Each sealing portion may individually form a seal between the outer wall of the catheter and the brain structure. If a surface defect causes one sealing portion to fail, additional downstream sealing portions in the direction of the proximal end of the catheter may retain the substance to be administered. Such a configuration provides a redundancy in the seal.

Radially circumferential cavities, recesses, or recessed portions may be formed between or by the bumps. These cavities, et al. can form "collecting points" for the substance and can prevent backflow.

A profile may be formed within one or more partial portions or, viewed as a whole, one profile may be formed that includes a plurality of partial portions. Depending on each profile's of configuration's intended use, a variety of configurations can be used in tissue structures having different material properties.

Partial portions of the catheter can be made of the catheter material or can be made of another material that changes its volume. The volume changing material may be used in the partial portions from which the subsequent sealing portions are formed. The outermost distal end of the catheter can be made of a material other than the material of these partial portions.

Partial portions and/or partial regions between the partial portions can have different dimensions along the longitudinal axis of the catheter. The different dimensions enable different surface profiles to be formed depending on the purpose, aim, and use of the catheter. The different dimensions of the portions and the different surface profile may extend over the entire length of the catheter.

One or more of the partial portions can have different relative changes in volume, such that the partial portion volumes can vary over the length of the catheter. Different partial portions can have volume changes of different magnitudes. Such volume changes may be achieved by using different concentrations of the material that changes its volume in the partial portions. The different changes in volume also may be achieved by using different materials or material compositions that exhibit different increases in volume.

A profile that does not have mirror symmetry with a plane through a longitudinal axis of the catheter (e.g., a screw-like profile) also can be formed on the outer wall of the catheter. A threaded or screw-like profile also enables the catheter to be "unscrewed" from the brain tissue after use. Such removal can be achieved without damaging adjacent brain tissue.

The change in the volume of the material also can be achieved by physical or chemical ambient conditions and/or influencing factors in the vicinity of the material. The conditions and factors and volume changing materials can include:

- changes in voltage and/or current (the material can be, for example, polymer hydrogel based on polyacrylic acid/poly (vinyl sulfonic acid));
- changes in pH value (the material can be, for example, Polyelectrolyte Hydrogels such as hydroxypropyl methacrylate (HPMA), N,N-dimethylaminoethyl methacrylate (DMA) or tetraethylene glycol dimethacrylate (TEGDMA));
- changes in the concentration of ions;
- changes in light intensity and/or light wavelength;
- changes in the presence of water (the material can be, for example, hydro-gels);
- changes in the electromagnetic field (the material can be, for example, polymer hydrogel based on polyacrylic acid/poly(vinyl sulfonic acid));
- changes in temperature (the material can be, for example, poly(methacryloyl L-alanine ethyl ester) hydrogel or poly(N-isopropylacryamide));
- changes in the concentration of chemical elements and/or compounds (the material can be, for example, stimuli-responsive hydro-gels); or
- a combination of the above.

The changed conditions can be changes that are caused by the presence of bodily ambient conditions in the administering environment. The changed conditions also can be changes that are caused by the presence of the substance to be administered, e.g., when the substance is introduced through the catheter.

BRIEF DESCRIPTION OF THE DRAWINGS

The forgoing and other features of the invention are hereinafter discussed with reference to the figures.

DETAILED DESCRIPTION

Figure 1:
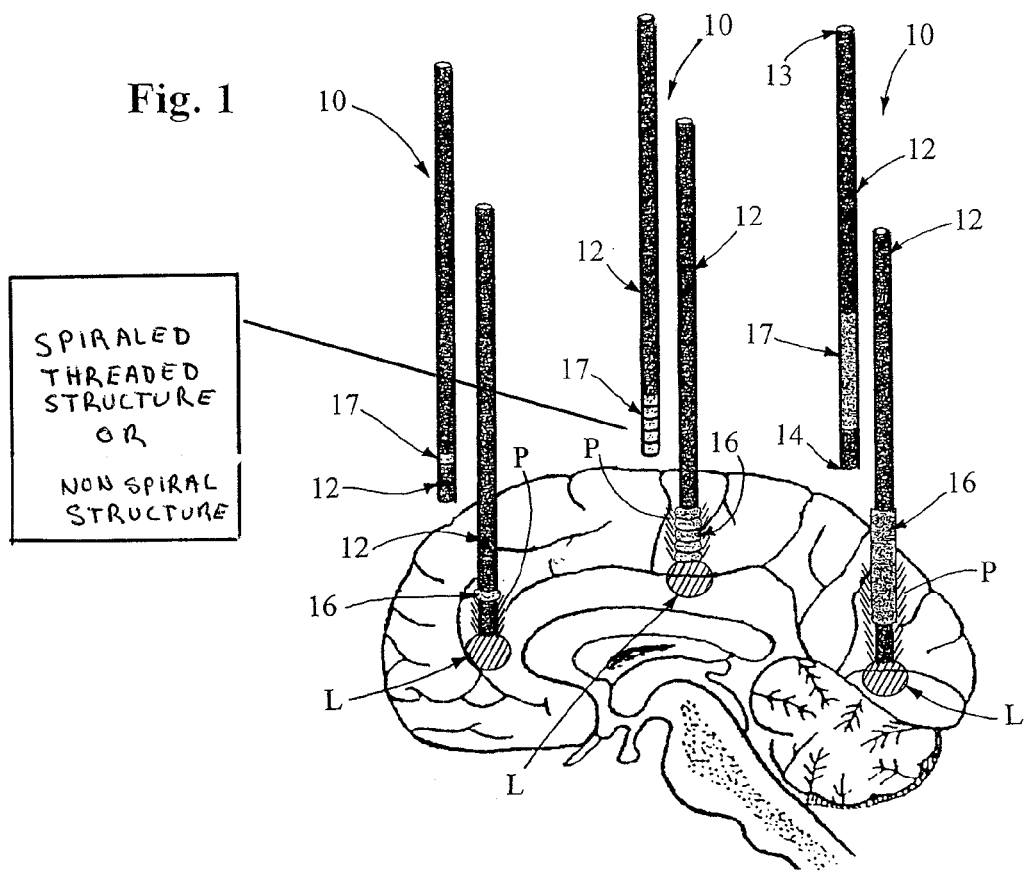
FIG. 1 illustrates different exemplary catheters, both in their initial shape before the change in volume and in their final shape after the change in volume.

Exemplary catheters 10 shown in FIG. 1 include a catheter body 12 including a proximal end 13 and a distal end 14. To administer a liquid substance into a body tissue (in this example a brain tissue), the distal end 14 of the catheter body 12 is inserted through a cranium into the brain tissue to the desired administering location L. Each catheter 10 has a lumen 15 formed by an interior surface of the catheter body 12. The substance to be administered may be introduced into the brain tissue through the lumen 15 (FIG. 2), from the proximal end 13 to the distal end 14, by applying a pressure at the proximal end 13.

Due to the applied pressure, once the substance exits the lumen 15 and disperses into the brain tissue, a portion of the substance attempts to flow back along the exterior of the catheter body 12 from the administering location L. The substance flows through a pathway P created in the brain tissue by the insertion of the catheter 10. Pathway P is essentially a gap between the outer surface of the catheter body 12 and the brain tissue. For proper treatment, any backflow should be minimized because the computer-assisted simulations of the dispersion used to plan the treatment generally require a point source delivery of the substance rather than a backflow delivery.

Figure 2:
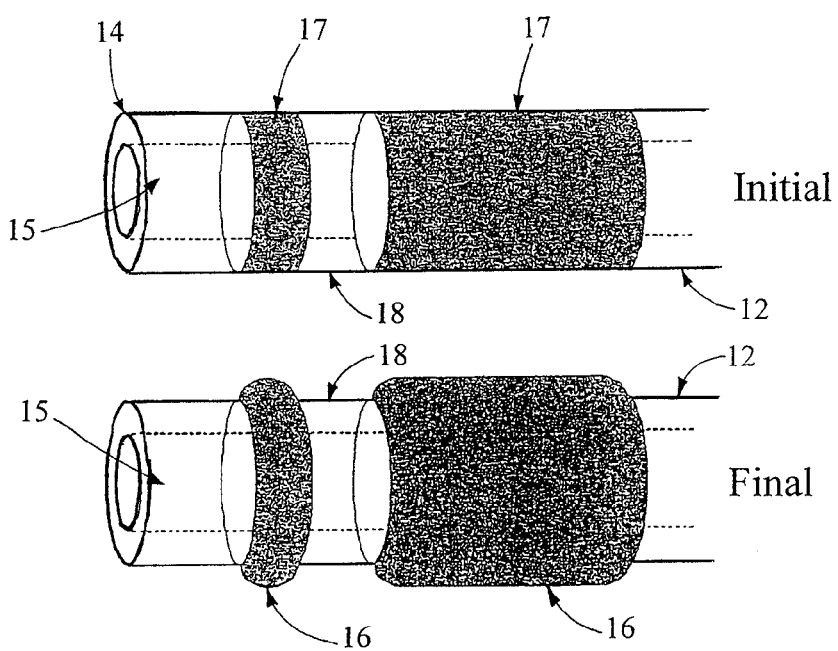
FIG. 2 illustrates a distal end of an exemplary catheter, both in its initial shape before the change in volume and in its final shape after the change in volume.

The backward flow or backflow can be prevented by providing sealing elements 16 on the catheter body 12, as shown in FIGS. 1 and 2. In the examples, one or more partial portions 17 are arranged on the catheter body 12, wherein these partial portions 17 include a material that is sensitive to changes in the ambient conditions. The sensitivity generates an increase in the volume of the partial portions 17, forming sealing elements 16 after the catheter 10 has been inserted into the brain structure. The partial portions 17 should be formed near the distal end 14 of the catheter body 12, to limit the backflow of the substance to be administered to as short a path length as possible. The partial portions 17 can form a defined structure or profile within themselves or, viewed globally, between each other. The defined structure or profile improves the sealing between the catheter body 12 and the brain structure.

Three example configurations are shown in FIG. 1 in their initial and final profiles. In the figures, catheters 10 have a generally constant cross-section of the catheter body 12 and then the partial portions 17 increase in volume and become sealing elements 16 after being introduced into the brain structure. As can be seen, the comparatively narrow catheter body 12 (with similarly sized partial portions 17) is inserted into the brain structure and, once exposed to the ambient conditions in the brain tissue, the partial portions 17 increase in volume to create the sealing elements 16 in several different profiles and configurations.

In the rightmost example of a catheter 10 in FIG. 1, a partial portion 17 is shown extending beyond the brain structure. In this manner, the partial portion 17 once expanded into a sealing element 16, can form a seal even if the administering location L is near an outer cerebral membrane.

FIG. 2 depicts the initial and final profiles of the distal end 14 of the catheter 10 including two partial portions 17 made of a material that changes in volume. Extending between the expanding material partial portions 17 are partial portions 18 that are made of a different material, such as the catheter material. As noted above, the catheter body 12 encloses a lumen 15 through which the substance to be administered is introduced into the brain tissue. The lower representation in FIG. 2 also shows how the volume of the partial portions 17 has increased in the final state, e.g., after the catheter has been placed into the brain structure. Upon expanding, the partial portions 17 become sealing elements 16 and operate to seal the pathway P between the outer surface of the catheter body 12 and the brain structure.

A configuration that incorporates a plurality of partial portions 17 in connection with non-expanding partial portions 18 shown in FIG. 2 wherein a cavity or space is formed between the sealing elements 16. FIG. 1 also shows a partial portion 17 that expands into a sealing element 16 having a complex profile (middle example of FIG. 1). The use of multiple sealing elements or complex profile sealing elements may further obstruct the backflow of the substance. Should the substance overcome the first sealing element (viewed from the distal end), it then enters a "collecting space" formed between the two sealing elements 16 (or in a cavity formed by the complex profile). The arrangement of these flow obstructions can be repeated as often as desired, such that the backflow of the substance to be administered is reduced to a minimum. The flow obstruction also can be varied or increased by the length of the sealing element(s) 16.

Although the invention has been shown and described with respect to a certain preferred embodiment or embodiments, it is obvious that equivalent alterations and modifications will occur to others skilled in the art upon the reading and understanding of this specification and the annexed Figures. In particular regard to the various functions performed by the above described elements (components, assemblies, devices, software, computer programs, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A catheter for administering a substance into a body tissue, comprising:
    a lumen;
    an elongated catheter body surrounding said lumen, said catheter body having a longitudinal axis; and
    a sealing member attached to said catheter body, said sealing member operable to change volume in response to ambient conditions from an unexpanded condition to an expanded condition forming a profiled outer surface of the catheter, the sealing member comprising a plurality of discrete longitudinally spaced apart sealing portions, wherein when the sealing member is in the unexpanded condition an outer surface of at least two of the plurality of sealing portions have different lengths along the longitudinal axis of the catheter body.

2. The catheter according to claim 1, wherein the profiled outer surface of the catheter includes a plurality of raised partial portions.

3. The catheter according to claim 2, wherein the profiled outer surface of the catheter includes one or more non-raised or recessed partial portions.

4. The catheter according to claim 2, wherein the partial portions form a structure on the catheter body that does not have mirror symmetry with a plane through a longitudinal axis of the catheter body.

5. The catheter according to claim 4, wherein the partial portions form a spiral threaded structure.

6. The catheter according to claim 1, wherein the sealing member is comprised of a plurality of expandable partial portions that have at least two different materials or at least two different material compositions.

7. The catheter according to claim 1, wherein the profiled outer surface of the catheter is formed on and/or by a plurality of partial portions.

8. The catheter according to claim 7, wherein at least one of the plurality of partial portions is made of an expandable material different from an expandable material of other partial portions.

9. The catheter according to claim 7, wherein the partial portions that form the profiled outer surface have different shapes.

10. The catheter according to claim 7, wherein at least two of the plurality of the partial portions have different initial volumes of material and experience different changes in volume relative to each other.

11. The catheter according to claim 7, wherein at least two of the plurality of the partial portions comprise different materials or different material compositions, and the at least two of the plurality of partial portions experience different changes in volume relative to each other.

12. The catheter according to claim 1, wherein the sealing member's volume changes in response to physical or chemical influencing factors.

13. The catheter according to claim 1, wherein the sealing member's volume changes in response to one or more of the following influencing factors:
    changes in voltage and/or current;
    changes in pH value;
    changes in the concentration of ions;
    changes in the presence of water;
    changes in the electromagnetic field;
    changes in temperature;
    changes in the concentration of chemical elements or compounds; and
    changes in light intensity and/or light wavelength.

14. The catheter according to claim 1, wherein the sealing member's volume changes in response to the substance passing through the lumen.

15. The catheter according to claim 1, wherein the volume changing material is arranged along the catheter body in at least two different concentrations.

16. The catheter according to claim 1, wherein the plurality of sealing portions comprise at least three sealing portions, and the regions between the at least three sealing portions have different lengths along the longitudinal axis of the catheter.

* * * * *